United States Patent [19]

Rovnyak

[11] 4,128,647
[45] Dec. 5, 1978

[54] SUBSTITUTED THIAZOLO [3,2-a]-THIOPYRANO[4,3-d]PYRIMIDINES

[75] Inventor: George C. Rovnyak, Hopewell, N.J.

[73] Assignee: E. R. Squibb & Sons, Inc., Princeton, N.J.

[21] Appl. No.: 889,712

[22] Filed: Mar. 24, 1978

[51] Int. Cl.² .................... A61K 31/18; C07D 409/14
[52] U.S. Cl. ..................... 424/251; 424/246; 542/449; 544/34; 544/252
[58] Field of Search ............... 542/449; 424/251, 246; 544/34, 250, 251, 252

[56] References Cited

U.S. PATENT DOCUMENTS

| 3,636,041 | 1/1972 | Schmidt et al. | 544/250 X |
| 3,657,245 | 4/1972 | Bormann et al. | 544/250 |

FOREIGN PATENT DOCUMENTS

| 4225916 | 5/1965 | Japan | 544/34 |
| 1242863 | 8/1971 | United Kingdom | 544/250 |

OTHER PUBLICATIONS

Khodzhibaev et al., "Reaction of CO with 4-Me-5-carbethoxy-2-Aminothiazole," in Chem. Abs. 85:21277r, 1976, vol. 85, p. 21285.

*Primary Examiner*—Allen B. Curtis
*Attorney, Agent, or Firm*—Lawrence S. Levinson; Merle J. Smith; Burton Rodney

[57] ABSTRACT

2,3,8,9-Tetrahydro-5H,6H-thiazolo[3,2-a]thiopyrano[4,3-d]pyrimidines of the structure

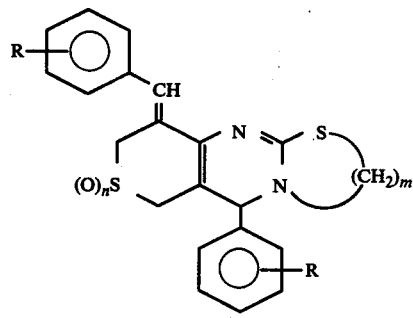

are provided wherein R is hydrogen, lower alkyl, halogen, acyl, cyano, carboxyl, trifluoromethyl or lower alkoxy, $n$ is 0 or 2 and $m$ is 2 or 3. These compounds are useful in the treatment of auto-immune disorders, such as rheumatoid arthritis.

11 Claims, No Drawings

SUBSTITUTED THIAZOLO [3,2-a]-THIOPYRANO[4,3-d]PYRIMIDINES

FIELD OF THE INVENTION

The present invention relates to substituted thiazolo[3,2-a]thiopyrano[4,3-a]pyrimidines and more particularly to 2,3,8,9-tetrahydro-5H,6H-thiazolo[3,2-a]thiopyrano[4,3-d]pyrimidines and their use in the treatment of auto-immune disorders, such as rheumatoid arthritis.

DESCRIPTION OF THE INVENTION

The 2,3,8,9-tetrahydro-5H,6H-thiazolo[3,2-a]thiopyrano[4,3-d]pyrimidines of the invention have the formula

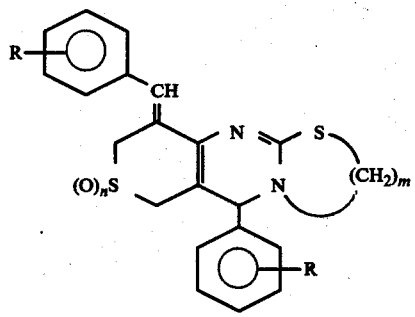

wherein R is hydrogen, lower alkyl, halogen, acyl, cyano, carboxyl, trifluoromethyl or lower alkoxy, $n$ is 0 or 2 and $m$ is 2 or 3.

Preferred are those compounds of formula I wherein $m$ is 2, $n$ is 0 or 2 and R is hydrogen or lower alkyl or lower alkoxy. In the most preferred embodiments, R is in the 2-position or 4-position of each of the phenyl rings.

The term "alkyl" and "alkoxy" as used herein (individually or as part of a larger group) refer to groups having 1 to 8 carbon atoms; alkyl and alkoxy groups having 1 to 3 carbon atoms are preferred.

The term "halogen" as used herein refers to fluorine, chlorine, bromine and iodine; fluorine and chlorine are preferred.

The term "acyl" as used herein refers to alkanoyl radicals of the structure

wherein R' is lower alkyl as defined above.

Compounds of formula I may be prepared by reaction of an unsaturated ketone of formula II with an amino compound of formula III employing a mole ratio of II:III of within the range of from about 1:1 to about 1:3, and preferably from about 1:1 to about 1:2. The reaction will be carried out in a suitable mixed organic solvent system, for example, a lower alkanol, such as n-butanol, and dimethyl sulfoxide (approximate 10:4 ratio) preferably at reflux temperature for periods ranging from 0.5 to 24 hours, and preferably from 2 to 4 hours.

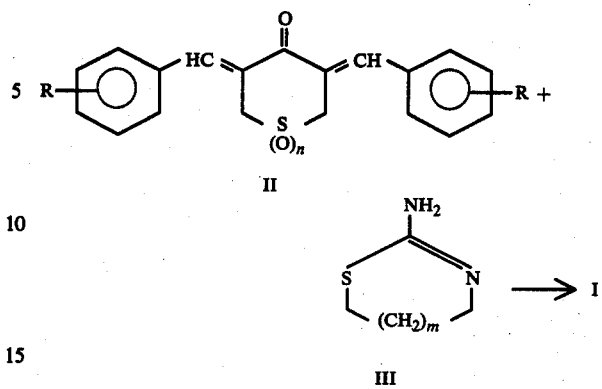

Alternatively, compounds of formula I may be formed by treatment of an intermediate aminol of formula IV with 1 to 2 equivalents of a Lewis acid, preferably TiCl₄, in an aprotic solvent, such as toluene, while heating at reflux temperature for from 0.5 to 2 hours.

The intermediate aminol IV may also be cyclodehydrated to I by heating in a mixture of n-butanol and DMSO (preferably in a ratio of 10:4) for from 0.5 to 24 hours, preferably for from 2 to 4 hours.

Compounds of formula IV are prepared by reacting, as above, an amino compound of formula III with an unsaturated ketone of formula II, but under milder conditions such as performing the reaction in a solvent in which the formed aminol IV is sparingly soluble. The preferred solvent is acetone or methyl ethyl ketone but a chlorinated solvent such as chloroform may also be used, and the preferred temperature for this reaction is ambient although heating at reflux temperature is sometimes necessary.

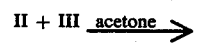

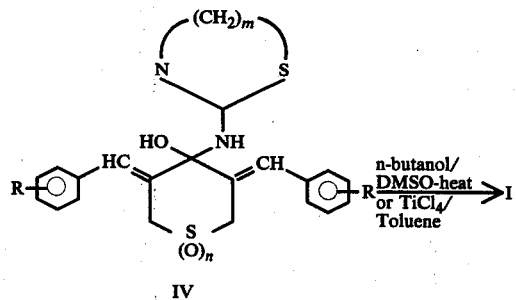

Unsaturated ketones of formula II are prepared as described in J.A.C.S., 79, 156 (1957). Amines of formula III are obtained either commercially ($n=2$) or are prepared ($n=3$) as described in J.O.C., 31, 2349 (1966).

The compounds of formula I form acid-addition salts with inorganic and organic acids. These acid-addition salts frequently provide useful means for isolating the products from reaction mixtures by forming the salt in a medium in which it is insoluble. The free base may then be obtained by neutralization, e.g., with a base such as sodium hydroxide. Any other salt may then be formed from the free base and the appropriate inorganic or organic acid. Illustrative are the hydrohalides, especially the hydrochloride and hydrobromide, sulfate, nitrate, phosphate, borate, acetate, tartrate, maleate, citrate, succinate, oxalate, benzoate, ascorbate, salicylate, methanesulfonate, benzenesulfonate, toluenesulfonate and the like. Preferred salts are the hydrochlorides and maleates.

The compounds of the invention have antiinflammatory activity as measured by the mouse active arthus (MAA) test and are useful as antiinflammatory agents and are effective in the prevention and inhibition of granuloma tissue formation in warm blooded animals, and may be used, for example, in a manner similar to phenylbutazone or indomethacin. They may be used to decrease joint swelling, tenderness, pain and stiffness in mammalian species, such as dogs and monkeys, e.g., in conditions such as rheumatoid arthritis. Compounds of formula I or a physiologically acceptable acid-addition salt thereof may be compounded for such use according to accepted pharmaceutical practice in oral dosage forms such as tablets, capsules, elixirs or powders or in injectable form for administration of about 100 mg to 2 gm per day, preferably 100 mg to 1 gm per day in two to four divided doses.

The following examples further illustrate and represent preferred embodiments of the invention. All temperatures are expressed in degrees Centigrade.

EXAMPLE 1

2,3,8,9-Tetrahydro-5-(4-methoxyphenyl)-9-[(4-methoxyphenyl)methylene]-5H,6H-thiazolo[3,2-a]thiopyrano[4,3-d]pyrimidine A mixture of tetrahydro-3,5-bis[(4-methoxyphenyl)-methylene-4H-thiopyran-4-one (4.9 g, 14 mmole) and 2-amino-2-thiazoline (1.8 g, 17.6 mmole) in acetone (300 ml) is heated at reflux temperature overnight. The precipitate (4.7 g) collected is a mixture of starting ketone and intermediate aminol (4-[(4,5-dihydro-2-thiazolyl-)amino]tetrahydro-3,5-bis[(4-methoxyphenyl)methylene]thiopyran-4-ol) in a ratio of 4:6.

The precipitate collected above is then dissolved in warm CHCl₃ solution, treated with an additional amount of 2-amino-2-thiazoline (1.8 g), and reheated at reflux temperature for 2 days. It is then warmed on a steam bath to evaporate off CHCl₃, acetone being added frequently to maintain the volume at about 150-200 ml. When white needles start to appear, the mixture is cooled and filtered to give 3.1 g (51%) of product, m.p. 195°-197° C.

EXAMPLE 2

2,3,8,9-Tetrahydro-5-phenyl-9-(phenylmethylene)-5H,6H-thiazolo[3,2-a]thiopyrano[4,3-d]pyrimidine

A.

4-[(4,5-Dihydro-2-thiazolyl)amino]tetrahydro-3,5-bis-(phenylmethylene)-2H-thiopyran-4-ol A slurry of tetrahydro-3,5-bis-(phenylmethylene)-4H-thiopyran-4-one (5.5 g, 18.9 mmole) in 200 ml of acetone is treated with a solution of 2-amino-2-thiazoline (2.0 g, 19.6 mmole, filtered) in 100 ml of acetone at room temperature. The mixture never becomes homogeneous, but the nature of the solids change (yellow to white). After stirring at room temperature for 2 days, the starting ketone remains as evidenced by tlc. Additional 2-amino-2-thiazoline (1 g, 9.8 mmole, filtered) in 50 ml of acetone is added and the mixture is heated at reflux temperature for 1 day. Upon cooling to room temperature, filtration and washing with acetone affords a combined yield of 6.9 g (92.5%) of product in two crops, m.p. 171°-172.5°).

B.

2,3,8,9-Tetrahydro-5-phenyl-9-(phenylmethylene)-5H,6H-thiazolo[3,2-a]thiopyrano[4,3-d]pyrimidine A slurry of the 4-[(4,5-dihydro-2-thiazolyl)amino]tetrahydro-3,5-bis(phenylmethylene)-2H-thiopyran-4-ol (2.0 g, 5.1 mmole) from part A in 20 ml dry toluene under nitrogen at room temperature is treated with 12 ml of a solution of TiCl₄ in toluene (1.29 g, TiCl₄ in 25 ml). The resulting mixture is heated at reflux temperature for 2 hours. Upon cooling, the solid mass is pulverized and collected by filtration. The solids are partitioned between CHCl₃ and aqueous NaHCO₃. The aqueous layer is extracted with additional CHCl₃. The extracts are washed (H₂O), combined, dried (CaCl₂) and concentrated on a steam bath; a volume of 75-100 ml is maintained by periodic addition of MeOH. When precipitation commences, the flask is cooled to room temperature. The product is collected, washed (MeOH) and dried in vacuo (80°) for several hours to give 1.5 g (79%) of product, m.p. 195°-196° d.

EXAMPLE 3

2,3,8,9-Tetrahydro-5-phenyl-9-(phenylmethylene)-5H,6H-thiazolo[3,2-a]thiopyrano[4,3-d]pyrimidine, maleate salt (1:1)

A suspension of 2,3,8,9-tetrahydro-5-phenyl-9-(phenylmethylene)-5H,6H-thiazolo[3,2-a]thiopyrano[4,3-d]pyrimidine (3.0 g, 0.0079 mole) in 25 ml of MeOH is treated with 0.92 g (0.0079 mole) of maleic acid. The solution is evaporated in vacuo to give an oil which gradually solidifies. The yield is 3.7 g, m.p. 142°-144°. Crystallization from 15 ml of MeCN gives 3.0 g (77%) of cream colored product, m.p. 143°-145°.

EXAMPLE 4

2,3,8,9-Tetrahydro-5-phenyl-9-(phenylmethylene)-5H,6H-thiazolo[3,2-a]thiopyrano[4,3-d]pyrimidine,7,7-dioxide

A.

4-[(4,5-Dihydro-2-thiazolyl)amino]tetrahydro-3,5-bis-(phenylmethylene)-2H-thiopyran-4-ol,-1,1-dioxide A stirred solution of tetrahydro-3,5-bis-(phenylmethylene)-4H-thiopyran-4-one-1,1-dioxide (6.5 g, 20 mmole) in 150 ml of CHCl₃ is heated at reflux temperature while a solution of 2-amino-2-thiazoline (3.1 g, 30 mmole) in 150 ml of CHCl₃ (filtered) is added. The solution is allowed to concentrate to ca. 150 ml and then left at room temperature for 20 hours. The solids are collected, washed with fresh CHCl₃ and hexane and dried in vacuo at 100° for 5 hours to give 6.5 g (76%) of product, m.p. 176°-177°.

B.

2,3,8,9-Tetrahydro-5-phenyl-9-(phenylmethylene)-5H,6H-thiazolo[3,2-a]thiopyrano[4,3-d]pyrimidine,-7,7-dioxide A slurry of aminol 4-[(4,5-dihydro-2-thiazolyl-)amino]tetrahydro-3,5-bis(phenylmethylene)-2H-thiopyran-4-ol-1,1-dioxide (from part A, 4.26 g, 10 mmole) in 100 ml of dry toluene under nitrogen at room temperature is treated with 11 ml of a solution of TiCl₄ in toluene (5.185 g TiCl₄ in 50 ml). The mixture is then heated at reflux temperature for 1.5 hours. Upon cooling, the solids are collected and partitioned between CHCl₃ and aqueous NaOH; the aqueous layer is extracted with fresh CHCl₃. The extracts are washed (H₂O), combined, dried (CaCl₂) and concentrated on a steam bath; a volume of 100–125 ml is maintained by periodic addition of MeOH. When crystallization commences, the flask is cooled to room temperature. The product is collected, washed (MeOH) and dried in vacuo (80°) for several hours to give 3.6 g (88%) of product, m.p. 230° d.

EXAMPLE 5

2,3,8,9-Tetrahydro-5-(4-methylphenyl)-9-[(4-methylphenyl)-methylene]-5H,6H-thiazolo[3,2-a]thiopyrano[4,3-d]pyrimidine

A.

4-[(4,5-Dihydro-2-thiazolyl)amino]tetrahydro-3,5-bis[(4-methylphenyl)methylene]thiopyran-4-ol To a stirred suspension of tetrahydro-3,5-bis-(4-methylphenylmethylene)-4H-thiopyran-4-one (5 gm; 15.6 mmole) in acetone (150 ml) is added a freshly filtered solution of 2-amino-2-thiazoline (1.9 gm, 18.6 mmole) in acetone (100 ml).

The mixture is heated at reflux temperature for 32 hours. Although it does not become homogeneous during heating, the appearance of the insoluble solids changes from yellow to white. The mixture is then cooled overnight.

Solids are collected by filtration and washed well with acetone to yield 5 gm (76%) of product, m.p. 189°–191° C.

B.

2,3,8,9-Tetrahydro-5-(4-methylphenyl)-9-[(4-methylphenyl)methylene]-5H,6H-thiazolo-[3,2-a]thiopyrano[4,3-d]pyrimidine To a stirred suspension of 4-[(4,5-dihydro-2-thiazolyl)-amino]tetrahydro-3,5-bis[(4-methylphenyl)-methylene]thiopyran-4-ol (from Part A) (2.5 gm; 5.9 mmole) in dry toluene (120 ml), is added slowly a solution of titanium tetrachloride (0.56 gm; 3.0 mmole) in toluene (5.4 ml). The orange mixture is heated at reflux temperature for 1.5 hour. After it is cooled, the solid is pulverized and filtered.

The crude solid is dissolved in CHCl₃ and washed with dilute NaOH solution and H₂O. The organic phase is dried and concentrated in vacuo to give 1.9 gm of a foamy residue. This is applied to a silica gel column. The fraction eluted with 0–5% ethyl acetate/CHCl₃ are combined, concentrated and the residue crystallized from MeOH to to give 1.2 gm (50%) of product, m.p. 173°–175° C. (d).

EXAMPLE 6

2,3,8,9-Tetrahydro-5-(2-methoxyphenyl)-9-[(2-methoxyphenyl)methylene]-5H,6H-thiazolo[3,2-a]thiopyrano[4,3-d]pyrimidine, 7,7-dioxide

A.

Tetrahydro-3,5-bis(2-methoxyphenylmethylene)-4H-thiopyran-4-one-1,1-dioxide

A stirred solution of tetrahydro-1,4-thiapyrone-1,1-dioxide (5.0 g, 0.033 mole) in 75 ml of EtOH is treated with 9.3 g (0.068 mole) of o-anisaldehyde and 5 ml of HOAc/piperidine (2:1 v.v). After heating at reflux for 16 hours, the mixture is cooled and the yellow product is filtered and washed with EtOH to give 7.6 g (58%) of material, m.p. 198°–200°.

B.

2,3,8,9-Tetrahydro-5-(2-methoxyphenyl)-9-[(2-methoxyphenyl)methylene]-5H,6H-thiazolo-[3,2-a]thiopyrano[4,3-d]pyrimidine, 7,7-dioxide A mixture of tetrahydro-3,5-bis(2-methoxyphenylmethylene)-4H-thiopyran-4-one-1,1-dioxide (8.0 g, 0.020 g) and 2-amino-2-thiazoline (2.9 g, 0.023 mole) in 100 ml of n-BuOH and 40 ml of DMSO is stirred and heated at reflux for 1 hour. The solution is cooled and the solvents are evaporated in vacuo to give a viscous oil. Trituration of this material with EtOH then with ether gives 6.7 g of a tan solid, m.p. 70°–74° dec.

The above material is dissolved in a small amount of CH₂Cl₂ and chromatographed over 125 g silica gel. Elution with 6 × 200 ml of 75% CH₂Cl₂/toluene gives 5.0 g (53%) of product, m.p. 80°–84° dec.

EXAMPLE 7

2,3,8,9-Tetrahydro-5-(4-methoxyphenyl)-9-[(4-methoxyphenyl)-methylene]-5H,6H-thiazolo[3,2-a]thiopyrano[4,3-d]pyrimidine-7,7-dioxide

A.

4-[(4,5-Dihydro-2-thiazolyl)amino]tetrahydro-3,5-bis[(4-methoxyphenyl)methylene]thiopyran-4-ol-1,1-dioxide A stirred solution of tetrahydro-3,5-bis(4-methoxyphenylmethylene)-4H-thiopyran-4-one-1,1-dioxide (5.7 g, 0.014 mole) in 100 ml of MEK is treated with 2-amino-2-thiazoline (2.1 g, 0.020 mole). After heating at reflux for 1 hour the yellow mixture becomes colorless. After cooling for several hours, the product is filtered and washed with MEK and ether to give 7.0 g (97%) of colorless product, m.p. 194°–196°.

B.

2,3,8,9-Tetrahydro-5-(4-methoxyphenyl)-9-[(4-methoxyphenyl)methylene]-5H,6H-thiazolo[3,2-a]thiopyrano[4,3-d]pyrimidine-7,7-dioxide A suspension of 4-[(4,5-dihydro-2-thiazolyl)amino]-tetrahydro-3,5-bis[(4-methoxyphenyl)methylene]thiopyran-4-ol-1,1-dioxide (6.0 g, 0.012 mole) in 75 ml of n-BuOH and 25 ml of DMSO is stirred and heated at reflux for 1 hour. The volume of the resulting solution is reduced by approximately one-half using a Dean-Stark trap. After cooling, the yield of yellow product is 4.7 g, m.p. 235°–240°. Crystallization from 25 ml of DMF gives 4.0 g (69%) of cream colored product, m.p. 243°–245°.

EXAMPLES 8 to 21

Following the procedure of Example 1, except substituting for tetrahydro-3,5-bis-(4-methoxyphenyl)-methylene-4H-thiopyran-4-one, the compound shown in Column I of Table I set out below, and substituting for 2-amino-2-thiazoline, the compound shown in Column II, the product shown in Column III is obtained.

TABLE I

| Column I | Column II | Column III |
|---|---|---|

[Column I: bis-benzylidene thiopyranone structure with R-phenyl groups and S in ring]
[Column II: 2-amino-thiazoline/thiazine structure with NH₂, S, N, (CH₂)ₘ]
[Column III: fused product structure with R-phenyl groups, S, N, (CH₂)ₘ]

| Ex. No. | R(position) | m | R(position) | m |
|---|---|---|---|---|
| 8. | CH₃(4) | 3 | as in Column I | as in Column II |
| 9. | Cl(3) | 2 | | |
| 10. | CH₃C(4) (with =O) | 2 | | |
| 11. | CN(4) | 2 | | |
| 12. | COOH(4) | 2 | | |
| 13. | CF₃(4) | 2 | | |
| 14. | C₂H₅O(2) | 3 | | |
| 15. | Br(4) | 3 | | |
| 16. | Cl(2) | 3 | | |
| 17. | C₂H₅C(2) (with =O) | 3 | | |
| 18. | CN(2) | 3 | | |
| 19. | COOH(3) | 3 | | |
| 20. | CF₃(3) | 3 | | |
| 21. | C₃H₇O(4) | 3 | | |

EXAMPLES 22 to 34

Following the procedure of Example 6, except substituting for tetrahydro-3,5-bis(2-methoxyphenylmethylene)-4H-thiopyran-4-one-1,1-dioxide, the compound shown in Column I of Table II set out below, and substituting for 2-amino-2-thiazoline, the compound shown in Column II, the product shown in Column III is obtained.

TABLE II

| Column I | Column II | Column III |
|---|---|---|

[Column I: bis-benzylidene thiopyranone 1,1-dioxide structure with SO₂]
[Column II: 2-amino-thiazoline structure with NH₂, S, N, (CH₂)ₘ]
[Column III: fused product with O₂S, N, S, (CH₂)ₘ and R-phenyl groups]

| Ex. No. | R(position) | m | R(position) | m |
|---|---|---|---|---|
| 22. | C₂H₅(4) | 3 | as in Column I | as in Column II |
| 23. | Br(3) | 2 | | |
| 24. | CH₃C(4) (with =O) | 2 | | |
| 25. | CN(2) | 2 | | |
| 26. | COOH(3) | 2 | | |
| 27. | CF₃(4) | 2 | | |
| 28. | C₂H₅O(3) | 3 | | |
| 29. | Cl(4) | 3 | | |
| 30. | CH₃C(4) (with =O) | 3 | | |
| 31. | CN(2) | 3 | | |
| 32. | COOH(4) | 3 | | |
| 33. | CF₃(4) | 3 | | |

TABLE II-continued

| | Column I | Column II | Column III |
|---|---|---|---|

| Ex. No. | R(position) | m | R(position) | m |
|---|---|---|---|---|
| 34. | C₃H₇O(4) | 3 | as in column I | as in column II |

What is claimed is:

1. A compound of the structure

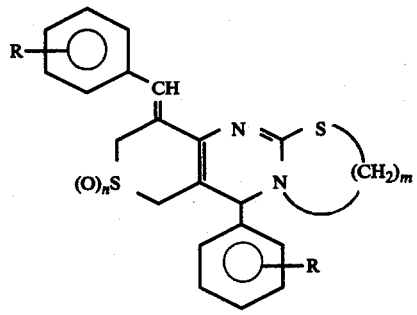

wherein R is hydrogen, lower alkyl, halogen, acyl, cyano, carboxyl, trifluoromethyl, and lower alkoxy, n is 0 or 2 and m is 2 or 3, and pharmaceutically acceptable salts thereof.

2. The compound of claim 1 wherein m is 2.

3. The compound of claim 1 wherein R is hydrogen, lower alkyl or lower alkoxy.

4. The compound of claim 1 wherein R is in the 2-position or 4-position, on each phenyl group.

5. The compound of claim 1 wherein m is 2, n is 0 or 2 and R is hydrogen, methyl or methoxy.

6. The compound of claim 1 having the name 2,3,8,9-tetrahydro-5-(4-methoxyphenyl)-9-[(4-methoxyphenyl)-methylene]5H,6H-thiazolo[3,2-a]thiopyrano[4,3-d]pyrimidine.

7. The compound of claim 1 having the name 2,3,8,9-tetrahydro-5-phenyl-9-(phenylmethylene)-5H,6H-thiazolo[3,2-a]thiopyrano[4,3-d]pyrimidine or its maleate salt, or its 7,7-dioxide.

8. The compound of claim 1 having the name 2,3,8,9-tetrahydro-5-(4-methylphenyl)-9-[(4-methylphenyl)methylene]-5H,6H-thiazolo[3,2-a]thiopyrano[4,3-d]pyrimidine or its 7,7-dioxide.

9. The compound of claim 1 having the name 2,3,8,9-tetrahydro-5-(2-methoxyphenyl)-9-[(2-methoxyphenyl)methylene]-5H,6H-thiazolo[3,2-a]thiopyrano[4,3-d]pyrimidine or its 7,7-dioxide.

10. A pharmaceutical composition for use in treating inflammatory conditions comprising an effective amount of an anti-inflammatory compound as defined in claim 1 and a pharmaceutically acceptable carrier therefor.

11. A method for treating an inflammatory condition in a mammalian host, which comprises administering to said host a therapeutically effective amount of a compound as defined in claim 1.

* * * * *